United States Patent
Baldwin et al.

(10) Patent No.: US 10,834,886 B2
(45) Date of Patent: Nov. 17, 2020

(54) SWITCHGRASS CULTIVAR PANIR

(71) Applicants: Brian S. Baldwin, Starkville, MS (US); Jason Brett Rushing, Newton, MS (US)

(72) Inventors: Brian S. Baldwin, Starkville, MS (US); Jason Brett Rushing, Newton, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 16/016,594

(22) Filed: Jun. 23, 2018

(65) Prior Publication Data
US 2019/0014734 A1 Jan. 17, 2019

Related U.S. Application Data

(60) Provisional application No. 62/524,251, filed on Jun. 23, 2017.

(51) Int. Cl.
*A01H 5/10* (2018.01)
*A01H 6/46* (2018.01)

(52) U.S. Cl.
CPC ............ *A01H 6/4642* (2018.05); *A01H 5/10* (2013.01)

(58) Field of Classification Search
None
See application file for complete search history.

(56) References Cited

U.S. PATENT DOCUMENTS

PP11,202 P  *  2/2000  Smith
8,319,009 B2 * 11/2012  Bouton ................... A01H 5/12
                                                    800/263

OTHER PUBLICATIONS

Mitchell, 2010, Bioenerg. Res., 3:321-327.*
Boe, 2003, Crop Science, 43:63-67.*
Liu et al, 2012, Bioenerg. Res., 5:662-668.*
Casler, 2012, "Chapter 2 Switchgrass Breeding, Genetics, and Genomis", Publications from USDA-ARS/UNL Faculty, 29-53.*

* cited by examiner

Primary Examiner — Jason Deveau Rosen
(74) Attorney, Agent, or Firm — Lawrence Arthur Schemmel

(57) ABSTRACT

A novel herbicide-resistant switchgrass cultivar, designated PanIR, is disclosed. The invention relates to the seeds of switchgrass cultivar PanIR, to the plants of switchgrass cultivar PanIR, and to methods for producing a switchgrass plant produced by crossing the cultivar PanIR with itself or another switchgrass variety. The invention relates to plant parts derived from switchgrass cultivar PanIR and to methods for producing other switchgrass cultivars, lines, or plant parts derived from switchgrass cultivar PanIR. The invention further relates to hybrid switchgrass seeds and plants produced by crossing the switchgrass cultivar PanIR with another switchgrass cultivar. It also further relates to other derivatives of the cultivar PanIR, methods of producing imazapic resistant switchgrass seeds and plants, and to producing commodity plant products.

27 Claims, No Drawings

SWITCHGRASS CULTIVAR PANIR

CROSS-REFERENCE TO RELATED APPLICATION

This application claims priority from U.S. Provisional Patent Application Ser. No. 62/524,251 filed Jun. 23, 2017. The entirety of the provisional application is incorporated herein by reference.

STATEMENT OF GOVERNMENT SUPPORT

This invention was made with government support under grant DE-FG36-06GO86025 awarded by the U.S. Department of Energy. The government has certain rights in the invention.

FIELD OF THE INVENTION

This invention relates to the field of grasses and more specifically to the field of switchgrass and a new cultivar of switchgrass that has natural resistance to herbicides.

BACKGROUND OF THE INVENTION

Selection for or against specific traits is a basic tenant of plant breeding. Reports in the literature exist where specific crop species have been screened (maize—Clearfield® corn, winter and spring wheat) and about spontaneous mutations of weedy species being found in fields sprayed with acetolactate synthase (ALS) inhibiting herbicides. Additionally, patents exist for transgenic crops containing a sequence making them resistant to imazapic. However, there has not existed until the present invention a deliberate screening for an improved cultivar of switchgrass for natural resistance to herbicides such as imazapic.

SUMMARY OF THE INVENTION

The present invention provides for a new cultivar of switchgrass that has naturally occurring herbicide resistance and tolerance. The new switchgrass cultivar has been given the experimental designation 'LL PANVI AL IR' (PanIR). The inventors have developed the improved cultivar of switchgrass having resistance to the imidazolinone herbicide imazapic (5-methyl-2-[4-methyl-5-oxo-4-(propan-2-yl)-4,5-dihydro-1H-imidazol-2-yl]pyridine-3-carboxylic acid) that can be used more efficiently as feedstock for biofuels and that allows this herbicide to be applied over the top of a mixture of the new cultivar PanIR and other imazapic-resistant native grass species.

After screening approximately 364,650 individuals of the publicly-released cultivar Alamo, seventy-eight (78) individuals survived the initial screening applying 8 oz/A of imazapic. A second screening was conducted, exposing the 78 individuals to the total allowable annual rate of imazapic in a one-time application (equivalent to 14 oz/A). Fifteen (15) of the first 78 either died or were stunted and dropped from the base population (resulting in 63 individuals). This base population is assembled as a crossing block at the Mississippi State University W.B. Andrews Agricultural Systems Research Facility (AKA MSU Agricultural Experiment Station). This base population and the subsequent generations were limited to derivations of the seven (7) most resistant to imazapic and were vegetatively propagated as the parents of a population of progeny that comprise the present invention. These individuals have naturally occurring resistance to imazapic arising from spontaneous mutations and are not transgenic. The inventors have assembled the novel individuals together to give rise to a new population of individuals resistant to imazapic from a switchgrass cultivar already adapted to the central and southern United States.

With the foregoing and other objects, features, and advantages of the present invention that will become apparent hereinafter, the nature of the invention may be more clearly understood by reference to the following detailed description of the preferred embodiments of the invention and to the appended claims.

DETAILED DESCRIPTION OF THE INVENTION

The present invention provides for a novel switchgrass cultivar that is naturally resistant to herbicides such as imazapic. The new switchgrass cultivar PanIR provides a novel cultivar of switchgrass that, as a result, is ideally suited for efficient processing into feedstock for biofuel production. The present invention comprises the most imazapic-resistant individual plants the inventors have selected which will be vegetatively propagated to generate a seedlot of imazapic-resistant progeny.

The invention contemplates or is comprised of the seeds of PanIR and plants grown from the seeds, as well as commodity products that comprise the plants or parts thereof. The invention is resistant to herbicides at such levels that generally or typically inhibit the growth of switchgrass plants. Specifically, the invention is resistant to imidazolinone herbicides including, for example, imazapic. The invention further involves a method of producing herbicide-resistant switchgrass plants from the seeds of the invention under conditions favorable for growing such plants and of producing switchgrass seeds from the plants. Still further, the invention encompasses materials including pollen and ovules of the PanIR plants. The methodology also includes applying imidazolinone herbicides, such as imazapic, at or near the plants of the invention to control weeds, and the like, such that the herbicide(s) inhibits the enzyme acetohydroxytacid synthase (AHAS) at a level that generally or typically inhibits the growth of a switchgrass plant.

The invention also encompasses tissue culture(s) of regenerable cells or protoplasts from or produced from the cultivar of the invention. A plant regenerated from such tissue would have all or essentially all the characteristics, i.e, physiological and morphological, of the cultivar of the invention. The regenerable cells and/or protoplasts are produced from a plant part tissue such as embryos, meristematic cells, pollen, cotyledon, hypocotyl, leaves, anthers, roots, root tips, pistils, flowers, seeds, glumes, panicles, and stems, for example, and protoplast produced from said tissue culture(s).

The invention encompasses a new cultivar that has resistance to herbicides, such as imazapic, used at a level that generally would inhibit switchgrass plant growth and a cultivar that is regenerated from such tissue culture(s) and that possesses all characteristics of PanIR and herbicide resistance.

The invention also involves a method of producing hybrid and enhanced switchgrass seed and plants that are imazapic resistant by crossing a first parent switchgrass plant with a second parent switchgrass plant, where the first and/or second parent is a plant of the cultivar PanIR, and harvesting the resultant hybrid switchgrass seed. The resultant hybrid switchgrass progeny plants are grown from the hybrid switchgrass seed and retain or possess imidazolinone herbicide resistance characteristic, or an enhanced level thereof, at a level that typically or generally inhibits switchgrass plant growth. Hybrid switchgrass seed is therefore produced utilizing this method of the invention and hybrid switchgrass progeny plants, or parts thereof, can be and are therefore grown therefrom and retain the herbicide resistance characteristic, such as to imazapic, at a level that typically inhibits switchgrass plant growth.

Such methodology encompasses crossing resultant hybrid switchgrass progeny plants with PanIR to produce additional new progeny plants, as well as repeating such crossing one or more times to produce selectively higher progeny plants. These higher progeny plants retain all the physiological and morphological characteristics of PanIR, as well as the same herbicide resistance(s) of PanIR. The methodology also comprises plants produced by the method, such that the plants have all the characteristics, both physiological and morphological, for example, of PanIR, as well as the herbicide resistance of PanIR to imazapic, for example.

Further, the invention also encompasses a method to produce a switchgrass cultivar that is derived from PanIR, wherein the method comprises the steps or process of crossing the PanIR plant with a second switchgrass plant to produce a resultant progeny plant that is therefore derived from PanIR. The method further involves (1) crossing the progeny plant that is derived from PanIR with itself or a second switchgrass plant to produce a seed, or seeds, of progeny plant of a subsequent generation, (2) growing the progeny plant of the subsequent generation from the seed, crossing the progeny plant of the subsequent generation with itself or a second switchgrass plant to produce a switchgrass plant derived from PanIR, and repeating the crossing of the resultant progeny plant and growing the progeny plant of the subsequent generation from seed steps above, i.e., (1) and (2), for at least one more generation to produce a switchgrass cultivar that is further derived from PanIR.

Additionally, the invention encompasses a method of introducing the desired or desirable trait of herbicide resistance, such as imazapic resistance, into a switchgrass plant, which involves or comprises crossing a PanIR cultivar or plant grown from a PanIR seed with another switchgrass plant that comprises or possesses the desired trait of imazapic resistance, for example, to produce F1 progeny plants, selecting one or more progeny plants having such desired trait to produce selected progeny plants, (a) crossing the progeny plants with switchgrass PanIR cultivars to produce backcross progeny plants, (b) selecting the backcross progeny plants that have such desired trait and all physiological and morphological characteristics of PanIR to produce selected progeny plants, and repeating (a) and (b) above three or more times in succession in order to produce selected fourth or higher backcross progeny plants comprising such desired trait (herbicide resistance, such as involving imazapic) as well as all or essentially all physiological and morphological characteristics of PanIR.

The method of the invention also encompasses producing a commodity plant product, whereby the method involves obtaining the cultivar PanIR, or a part thereof, and producing the commodity plant product from the plant or part thereof, such that the resultant product is biofuel feedstock, grass restoration material, and/or landscape or landscaping material, and the like.

The invention may enhance the establishment of switchgrass as a bioenergy crop and/or as a perennial grass in prairie restoration projects. Cross protection to other imidazolinone herbicides may also occur in the present invention as resistance is conferred by altered enzyme acetohydroxyacid synthase (AHAS) genes making enzyme receptors. Altered receptors preclude the entire class of herbicides from being effective. Such cross protection would mean that the switchgrass of the invention could tolerate other grass active ALS inhibiting herbicides including imidazolinone herbicides (imazamox, imazapic, imazapyr, and imazethapyr) and sulfylurea herbicides (metsulfuron methyl and sulfosulfuron). This ability would allow the useful controlling of a wide variety of weeds. As one example, cogongrass (*Imperata cylindrica*) is not susceptible to imazapic, but it is extremely susceptible to imazapyr. However, control with imazapyr is limited because germinating cogongrass seed have nothing to compete with and the herbicide kills plants that act as competitors as well. Seeding the cultivar of the present invention after a burn of cogongrass or after a herbicide spray application would allow competition between the resistant switchgrass and susceptible cogongrass.

Selection for Imazapic Herbicide Tolerance in Switchgrass

Abstract

Recurrent phenotypic selection (RPS) was used to screen and select Alamo switchgrass seedlings that showed resistance to imazapic herbicide at a rate of 245 grams active ingredient/hectare (g a.i./ha). Initial screenings of 364,650 seedlings resulted in 63 survivors, a selection intensity of 0.0172%. Subsequent testing of the next generation of seedlings indicated that multiple generations of selection were needed in order to transfer greater resistance to the offspring. Three generations of screening were used to identify seven parental clones resistant to high rates (about 14 oz/A) of imazapic.

Introduction

Switchgrass, along with other native warm season grasses (NWSGs), is hard to establish. Lack of weed control is the most serious limiting factor in establishment (Martin et al. 1981). Herbicides have the potential to selectively control problematic species in native warm-season grasslands. The inheritance of imidazolinone resistance and allelism of traits are all semi-dominant and unlinked. Higher levels of resistance can be achieved by stacking resistance genes into a single genotype. Winter wheat (*Triticum* spp.) has a single gene that has acceptable resistance, whereas spring wheat has two genes that are required for full resistance (Tan 2005). The advantages of combining imidazolinone resistant crops with imidazolinone herbicides allows the control of certain weeds that no other control method can provide. The system also controls a broad spectrum of weeds in several crops in which imidazolinone resistant varieties are available (Tan 2005). These perennial grasses, as seedlings, do not compete well with annual grass weeds and a large variety of broadleaf weeds. In pasture restorations, a mixture of NWSGs are often used. The species grown tend to be: big bluestem (*Andropogon gerardii*), little bluestem (*Schizachyrium scoparium*), indiangrass (*Sorghastrum nutans*), and switchgrass (*Panicum virgatum*). However, of the previously-mentioned species, switchgrass is the only one that is not imazapic resistant. Imazapic, marketed under the tradenames Plateau®, Journey®, and Cadre®, is used for prairie and pasture restorations. It is a selective herbicide useful for both the pre- and post-emergent control of selected annual and perennial grasses and some broadleaf weeds. Imazapic controls weeds by inhibiting of branched chain amino acid synthesis, and associated proteins. It is useful for weed control in natural areas, particularly with the establishment of NWSGs. While many options exist for broadleaf weed control in grasses, implementation of a weed control option that would remove weedy grasses from desirable grasses would give resistant species/cultivars an establishment advantage. Development of a cultivar of switchgrass that is resistant to imazapic would allow mixtures of NWSG and monocultures of this resistant switchgrass cultivar to be planted and weeds would be controlled allowing for more successful stands in the establishment year.

Literature Review

A major reason for stand failure of switchgrass is weed competition (Harper 2007). Removal of weeds through the use of appropriate practices or by the application of pre- and/or post-emergence herbicides can enhance establishment chances. Herbicides have the potential to selectively control problem species in NWSG plantings. Producers in the Great Plains have historically used 2,4-D and picloram to control broadleaf weeds (Fick and Peterson 1995).

Atrazine, a triazine herbicide, has been used to control annual grass and broadleaf weeds, especially in the South, and is especially effective in controlling pigweeds (*Amaranthus* sp.), yellow nutsedge (*Cyperus esculentus*), and quackgrass (*Elytrigia repens*). It can be applied preplant incorporated, preemergence, or early postemergence. Atrazine is often used in combination with the grass control herbicide metolachlor. Generally, mixing allows lower rates of atrazine to be used, which favors shorter soil persistence and reduces groundwater hazard. Atrazine is recommended for use in switchgrass because researchers have developed atrazine-tolerant cultivars of switchgrass and big bluestem in Nebraska (Mitchell and Britton 2000). Studies conducted at the Jamie L. Whitten Plant Materials Center in Coffeeville, Miss., have shown that atrazine has no deleterious effects on switchgrass stands. Unfortunately, atrazine is a restricted use pesticide (RUP) (Grabowski 2002). The Helena-manufactured product, Atrazine 4L, is not registered for use on switchgrass in Mississippi, but is allowed for use in Alabama, Florida, Georgia, and South Carolina (Helena Chemical Company 2007). While atrazine controls a wide variety of annual weeds in certain NWSG, some NWSG are susceptible as seedlings but tolerant once a crown has formed. Since chemical methods of weed control are limited due to the restriction of the use of atrazine on switchgrass and big bluestem, other mechanisms are being developed to control weed problems during establishment of NWSG. Atrazine is no longer labeled for rangeland use but must be investigated to evaluate the associated control with this herbicide. Species most susceptible include: Kentucky bluegrass (*Poa pratensis*), Canada bluegrass (*P. compressa*), smooth bromegrass (*Bromus inermis*), downy bromegrass (*B. tectorum*), green foxtail (*Setaria veridis*), annual bromes (*Bromus* spp.), and Russian thistle (*Salsola kali*). Some seedlings of some NWSG are not resistant to atrazine, but most established warm-season grass plants are not damaged by atrazine. Annual grasses such as crabgrass (*Digitaria sanguinalis*), fall panicum (*Panicum dichotomiflorum*), green foxtail, yellow foxtail (*Setaria glauca*), and barnyardgrass (*Echinochloa crusgalli*) usually cause the most significant threats to NWSGs during establishment (Mitchell and Britton 2000). Simazine has been used in the establishment of switchgrass. Pre-plant applications were applied to switchgrass cultivars, Alamo and Kanlow, in open field trials to determine herbicide effectiveness and to test agronomic weed management techniques (Minelli et al. 2004). Simazine was tested at a rate of 537 g a.i./ha along with other pre-emergent herbicides including terbuthylazine and pendimethalin. Preplant herbicides were evaluated based on selectivity of switchgrass in the number of emerged and viable plants in $m^{-2}$ and in terms of weed infestation. When compared with the untreated check, simazine and terbuthylazine caused a reduction of switchgrass stands ranging from 10-20%. Pendimethalin resulted in mortality of stands up to 50%, but was also the most effective in weed control (Minelli et al. 2004). Simazine is also not registered for any use in Mississippi, Alabama, Louisiana, or Georgia, but is registered for South Carolina and Kentucky (Drexel Chemical Company 2007).

Imidazolinone herbicides, which include imazapyr, imazapic, imazethapyr, imazamox, imazamethabenz, and imazaquin, control weeds by blocking the enzyme AHAS, which is needed for the biosynthesis of branched chain amino acids in plants. Imidazolinone resistance has been discovered as a naturally occurring genetic variant in maize, wheat (*Triticum aestivum*), rice (*Oryza sativa*), oilseed rape (*Brassica napus*), and sunflower (*Helianthus annuus*). Imidazolinone herbicides control a broad spectrum of grass and broad leaf weeds, have a low mammalian toxicity, and possess favorable environmental attributes. Imidazolinone-resistant crops contain AHAS alleles which produce enzymes in spite of the presence of the herbicide conferring resistance at the site of action for these crops (Tan et al. 2005). Imidazolinone-resistant maize was developed by tissue culture selection of cell callus on medium containing imazaquin. Commercial cultivars currently known as Clearfield® corn were produced as a result. Winter wheat (2n=6x=42) seed were treated with imazethapyr followed by a pre-emergence application. Four tolerant survivors were selected and used as parents to develop resistant wheat varieties marketed first in 2001 in France. Under the appropriate screening regime, resistance alleles (R) may be selected for even when present in a heterozygous individual (Foes et al. 1999; Hart et al. 1993; Sebastian et al. 1989; Wright and Penner 1998). This contrasts with selection against dinitroanilines where the r allele is recessive to the s allele (Jasieniuk et al. 1994; Zeng and Baird 1997). According to Tan et al. (2005) and Tranel and Wright (2002), ALS resistance follows normal Mendelian (nuclear) inheritance, therefore r ALS alleles are disseminated by both pollen and ovule. The genetics of ALS-inhibiting herbicide resistance is conferred by a single, dominant gene, which might partially account for the high frequency of resistance to ALS inhibitors found in weedy species (Tranel and Wright 2002). The amount of innate genetic variability of ALS-resistance in the population will affect the likelihood that R biotypes are selected by continuous application of ALS herbicides (Perez-Jones et al. 2007). Van Eerd et al. (2004) determined the genetics and inheritance of quinclorac and ALS-inhibitor (thifensulfuron) resistance in bedstraw (*Galium spurium*). Screenings indicated that quinclorac resistance was due to a single, recessive nuclear trait, based on a 1:3 ratio (resistant:susceptible) of the progeny of a controlled cross. Resistance to ALS inhibitors in bedstraw was due to a single, dominant nuclear trait, based on a 3:1 ratio (R:S). Genetic models were confirmed when $F_2$ plants survived quinclorac treatment and the resulting $F_3$ progeny segregated in a 1:0 ratio (R:S). In contrast, $F_3$ progeny separated into three resistance ratios for the ALS-inhibitor treatment: 1:0, 3:1, and 0:1 (R:S). This pattern indicates that either one of the $F_2$ parents was either heterozygous or homozygous for ALS-inhibitor resistance. DNA of common cocklebur (*Xanthium strumarium*) and common ragweed (*Ambrosia artemisiifolia*) were sequenced in a study by Jiang and Tranel (2002), which revealed that ALS resistance was highly variable in common ragweed, but not in common cocklebur. Regardless of the level of variability for ALS resistance within a population, high ALS variability does not ensure that R ALS alleles will be expressed (Tranel and Wright 2002). This being said, R ALS allele accumulation in a population of switchgrass was assumed to be dominant. According to this research, dominant alleles would enable selection for this trait to occur at a faster rate compared to selection for recessive alleles. However, a study was conducted on ALS resistance in Palmer amaranth (*Amaranthus palmeri*) and common waterhemp (*A. rudis*) to determine the spread of resistance across species (Franssen et al. 2001). Approximately 3,500 hybrid seedlings (*A. palmeri*×*A. rudis*) were screened using PCR (polymerase chain reaction) fragments. Of the seedlings screened, only 35 were confirmed as hybrids conferring herbicide resistance as a phenotypic and molecular marker (selection intensity of 1%). The advantages of combining imidazolinone resistant crops with imidazolinone herbicides allow the control of certain weeds when no other control method is available. This system also controls a broad spectrum of weeds in several crops in which imidazolinone-resistant varieties are available. Since herbicides with ALS-inhibiting sites of action are the most widely used in the world, they have become notorious for their ability to create resistant weed populations (Tranel and Wright 2002). This wide use has resulted in more weed species resistant to imidazolinones than any other herbicide group. Cases of resistance that have been serendipitously discovered usually occur due to natural selection of plants with spontaneously altered ALS allele enzymes caused by widespread and repeated use of these herbicides. The strong selection pressure exerted on the weed populations result in only resistant genotypes remaining to reproduce. Selection pressure occurs due to high herbicide activity on sensitive biotypes at the rates used, the amount of residue in the soil, and the vast acreage treated with the same herbicide family (Tranel and Wright 2002).

Imazapic (formerly known as imazameth or AC 263,222), is marketed under the tradenames Plateau®, Journey® and Cadre®, and is manufactured by BASF. These products are sold as soluble liquid (SL) or dispersible granule (DG) formulations. Cadre® is used for application on peanut crops (Tu et al. 2004). Plateau® is an ALS-inhibitor herbicide that may be applied to newly established or existing stands of labeled species in areas such as pastures, rangeland, CRP land, and noncrop sites such as roadsides, industrial sites, prairie restoration sites, drainage ditch banks, and other similar sites (BASF 2006). Imazapic selectively controls some annual and perennial broadleaves and grasses including cocklebur, buffalobur (*Solanum rostratum*), johnsongrass (*Sorghum halepense*), cheatgrass or downy brome (*Bromus tectorum*), bermudagrass (*Cynodon dactylon*), bahiagrass (*Paspalum nutatum*), smartweed (*Polygonum persicaria*), and leafy spurge (*Euphorbia esula*). In some cases, non-native weeds are more susceptible than desirable native species (Tu et al. 2004). Washburn and Barnes (2000) showed that the use of imazapic greatly reduced tall fescue to allow NWSGs to return in Kentucky grassland restoration projects. Cropland applications applied at 72 g a.i./ha controlled Johnsongrass, crabgrass, redroot pigweed (*Amaranthus retroflexus*), sicklepod (*Senna obtusifolia*), and morningglory (*Ipomoea* spp.) in corn (Wilcut et al. 1999). Post-emergence application combined with crop rotations of corn, peanut (*Arachis hypogaea*), and cotton (*Gossypium hirsutum*) controlled purple nutsedge (*Cyperus rotundus*) (Warren and Coble 1999). Imazapic is also known to suppress bahiagrass seedhead production (Baker et al. 1999). A study by Harper et al. (2004) showed the effects of Plateau® with five species of NWSG. Big bluestem, little bluestem, indiangrass, sideoats grama (*Bouteloua curtipendula*), and switchgrass were sown at 10.1 kg per ha (10 lbs PLS per acre) in separate, duplicate plots by broadcast and no-till methods in three locations in Tennessee: Middle Tennessee Expt. Stat., Highland Rim Expt. Stat., and Knoxville Expt. Stat. Plateau® was applied at the following treatments: pre-emergence at 140 g a.i./ha; pre-emergence at 210 g a.i./ha; post-emergence at 140 g a.i./ha; post-emergence at 210 g a.i./ha; control. Post-emergence applications were conducted at the 4-5 leaf stage. Switchgrass plots, whether drilled or broadcast, that received treatments contained fewer plants than the control plots (Harper et al. 2004). Salon and van der Grinten (1997) conducted a study using Plateau® as a pre- and post-emerge for the establishment of eastern gamagrass (*Tripsacum dactyloides*). The pre-emerge treatments (140 and 210 g a.i./ha) caused necrosis, followed by delayed emergence and stunted growth. A spray chamber was used to apply the post treatments (70, 140, and 210 g a.i./ha) which resulted in severe injury to the seedlings with a 0% survival at the 210 g a.i./ha rate (Salon and van der Grinten 1997). Imazapic is primarily degraded by soil microbial metabolism. It is moderately consistent in soils, is not known to move laterally through with surface water, and does not volatilize when applied in the field (Tu et al. 2004). Soil absorption increases with increasing pH.

Materials and Methods

Imazapic Resistant Switchgrass

Zero: First Generation Selection

Selection for herbicide resistance was conducted using methods similar to the study performed by Bahler and others (1983). Heavy duty plastic and metal trays measuring 51.5 cm×36.5 cm were used to hold the germinating seedlings during growth and also allowed for easy maintenance and efficient application of herbicide. The testing was conducted in a greenhouse that maintained a nightly temperature of 20° C. and a daily temperature of 30° C. Before the autumnal equinox, day length was not supplemented for the experiment. After the equinox, light was extended to 16 hrs. Day length is a concern due to switchgrass' photoperiodic nature. Eight trays represent a replicate, which were repeated over time. Each tray was filled with autoclaved field soil approximately ¾ full. A 2.5 cm×30.5 cm piece of PVC pipe was used to form ten micro-furrows spaced at 5 cm within each tray. Nine of the ten rows were planted with approximately 1500 Alamo switchgrass seed (Sharp Brothers, Healy, Kans.). The remaining, randomly selected row was planted with 250 indiangrass seed (MSU $3^{rd}$ cycle of selection for precocious germination). One hundred (100) seed were evenly dispersed within each furrow of the flat; flats were top-dressed with 0.63 cm of autoclaved field soil. The trays were watered on a daily basis. Emergence of the seedlings usually took place 6-8 days after planting. Once the seedlings broke the soil surface, they were allowed to grow to the three leaf stage (approximately 14 days). A calibrated spray chamber was used to apply the herbicide to the seedlings in the trays. For imazapic, the recommended rate is 140 g a.i./ha on mixed grassland, applied with less than 93.54 liters of water per hectare, sprayed at a constant pressure of 40 psi. A spray adjuvant (nonionic surfactant) was added to the formulation. In order to achieve the correct amounts for the spray mixture, the following calculations were made:

(8 fl.oz./1 ac.)×(1 ac./15 gal.sol.)×(1 gal./128 fl.oz-
  .sol.)×(20 f.oz.sol./1 bottle)×(3785 ml/128
  fl.oz.)=2.46 ml/1 bottle H$_2$O (3-1)

The formulation requires 2.46 mls of Plateau®, 1.5 mls of surfactant, and 556 mls of water to fill the spray bottle for the chamber. The trays were placed two at a time in the chamber and sprayed at a fixed speed (0.84 km/hr or 5.5 mph) to ensure proper dosage. A dose response curve was conducted on the sixth trial to determine the rate of Plateau® that would kill a majority of the switchgrass seedlings (Table 1).

TABLE 1

Dose response curve determining the rate of Plateau ® that would kill a majority of 'Alamo' switchgrass (*Panicum virgatum*) seedlings. Ratings are based on a scale of 1 to 5. Five represents death. Dosages are from 0 to 245 g a.i./ha.

| Rate | Date | | | | | | |
|---|---|---|---|---|---|---|---|
| (g a.i./ha) | 25-Sep | 3-Oct | 9-Oct | 16-Oct | 23-Oct | 30-Oct | 6-Nov |
| 0 | 0† | 0 | 0 | 0 | 0 | 0 | 0 |
| 35 | 0 | 1 | 1 | 2 | 3 | 4 | 4 |
| 70 | 0 | 1 | 1 | 2 | 3 | 4 | 4 |
| 105 | 0 | 1 | 2 | 3 | 4 | 5 | 5 |
| 140 | 0 | 1 | 2 | 3 | 4 | 5 | 5 |
| 175 | 0 | 1 | 2 | 4 | 4 | 5 | 5 |
| 210 | 0 | 1 | 2 | 4 | 4 | 5 | 5 |
| 245 | 0 | 1 | 2 | 4 | 4 | 5 | 5 |

†Ratings were conducted once a week for seven weeks.

The upper limit was 245 g a.i./ha, which exceeded the labeled rate for big bluestem and indiangrass. Trays were planted with eight micro-furrows of switchgrass, one row indiangrass (imazapic resistance check), and one row large crabgrass (susceptible check). Single trays were sprayed ranging from 35 to 245 g a.i./ha rates. One tray was not sprayed. Eight trays represented the curve and were assessed on the amount of discoloration relative to the unsprayed tray. Ratings were conducted once a week for seven weeks. Approximately 364,650 individuals were screened, resulting in 78 individual survivors (8 oz/A of Plateau®). A second screening was conducted, exposing those 78 individuals to the total allowable annual rate of Plateau® in a one-time application (14 oz/A). Fifteen of the first 78 either died or were stunted and dropped from the base population (now 63 individuals). This base population ($Cycle_1$ ) was assembled as a crossing block at the R.R. Foil Research Farm (33.469024, −88.784349). The second application of imazapic was applied to insure complete resistance and that no escapes were present. An isolated crossing block was established in the field with the seedlings being separated 400 m from other switchgrass crossing blocks. Seed was harvested from the crossing block from October to November, 2008. Since the seed ripened sequentially, a vacuum was used to remove only the seed from the panicle that had fully ripened. Analysis of variance to determine success of selection was conducted.

First: Second Generation Selection

Subsequent testing of the first generation seed/seedlings was conducted in the same manner as the initial herbicide screenings. The planting of the trays consisted of 8 rows of the first generation, one row Alamo, and one row indiangrass (tolerant control).

Seedlings of $Cycle_1$ (315,360) were screened for tolerance to 14 oz/A (2×) rate of Plateau®. Ninety-seven (97) survived the initial imazapic application. Sixty-eight (68) succumbed to a second (8 oz/A) application leaving twenty-nine (29) tolerant individuals which were planted in an isolated crossing block at Longview, Miss. (33.404999, −88.938283) as $Cycle_2$.

Second: Third Generation Selection

Selections of the second generation seed/seedlings were taken from a two-spray screening similar to the Zero: First Generation Selection. Seed was collected from $Cycle_2$ plants in the Fall of 2012. Seed of the Cycle 2 crossing block was germinated in flats. All seed was planted and screening commenced in two weeks. All material was screened with 16 oz/A (2.3×) rate of Plateau®. Of the approximate 300,000 seed germinated to seedlings, screened twice with the 16 oz/A rate, thirty-five (35) plants survived but only seven (7) showed no damage due to herbicide exposure. Each of those seven plants were cloned seven times to make up the base population for the population that comprises the present invention. An isolated crossing block of forty-nine (49) plants is presently being maintained at the Mississippi State University Agricultural Experiment Station, Starkville, Miss.

Results and Discussion

Development of Imazapic Resistant Switchgrass

Herbicide screening of seedlings produced from the first cycle polycross of selection showed a mortality rate greater than 75%, indicating that resistance displayed in the elite parental population (selected parents) did not completely transfer to the progeny. The inheritance of this trait to second cycle screenings may be attributed to a misconception of switchgrass genetics, faulty selection of the original parents, or foreign pollen contamination of the crossing block. In this disclosure, cycles are antecedent of the end product. $Cycle_0$, $Cycle_1$, $Cycle_2$, and $Cycle_3$ correspond to Alamo, PanIR I, PanIR II, and PanIR III, respectively. They are screening populations, except for PanIR III (the end product). Further, 'Syn' represents "synthetic", for a synthetic variety, and are future generations of the end product. Herein, the following are synonyms: $Syn_0$=PanIR III=Cycle III. Further, $Syn_1$ is the seed from the $Syn_0$ (PanIR III) block.

In the initial screenings for $Cycle_0$ (Alamo), 63 individuals were selected out of 306,000 seedlings (selection intensity of 0.0205%). During the screenings of $Cycle_1$, 29 seedlings were selected out of 36,441 seedlings (selection intensity of 0.0795%). This data suggests that at a low rate, herbicide resistance can spread throughout the species, similar to the Franssen et al. (2001) findings with inheritance of ALS resistance in *Amaranthus* spp.

The inventors did not observe intermediate resistance in the initial screening of Alamo. However, after the screening of $Cycle_0$, segregation into the semi-dominant ratios could be observed. Surviving individuals were separated into semi-resistant (poorseedling vigor; obvious signs of herbicide damage) and completely resistant (goodseedling vigor; little to no observed herbicide damage). A 2009 side-by-side comparison between Alamo and the $Cycle_0$ seed was conducted. Trays were sprayed with the recommended rate of Plateau® (35 g a.i./ha) and seedling counts were taken three weeks after application to assess the damage. Eight trays were planted with nine rows of $Cycle_0$ and a single row of Alamo. The average percentage survival for the seedlings per row was 2.98% for Alamo and 13.79% for $Cycle_0$.

Seedlings of $Cycle_1$ (315,360) were screened for resistance to 14 oz/A (2×) rate of Plateau®. Ninety-seven (97) survived the initial imazapic application. Sixty-eight (68) succumbed to a second (8 oz/A) application leaving 29 resistant individuals which were planted at Longview, Miss. (33.404999, −88.938283) as $Cycle_2$.

Seed was collected from $Cycle_2$ plants in the Fall of 2012. All seed was planted and screening commenced in two weeks. All material was screened with 16 oz/A (2.3×) rate of Plateau®. Of the approximate 300,000 seed germinated to seedlings, screening twice with the 16 oz/A rate reduced the number of survivors to seven. These seven individuals were grown in the greenhouse during the winter to increase crown size and each were subsequently divided into seven clones. Each set of clones was planted as a block on three-foot centers at the Andrews Plant Science Farm (33.470376, −88.763699) in a progressive advancement arrangement to generate Cycle$_3$ seed.

Three generations of screening with 2× (14 oz/A rate—Generation 0:1); 2× (14 oz/A rate—Generation 1:2); and 2.3× (16 oz/A rate—Generation 3) of Plateau® herbicide were required to produce the new cultivars of the present invention.

This novel variety of switchgrass is a 7-clone synthetic. With a limited number of parents (7) and obligate outcrossing of parents, a realistic number of generations of seed increase will probably be limited to two. PanIR Syn$_1$ seedlings are vigorous as volunteers and establish well. With an obligate outcrossing, species inbreeding depression does not occur. An increase in the degree of relationship among siblings manifests not as a loss of vigor, but as a reduction in the amount of seed produced per plant. Moreover, marketing/sale of certified seed of the invention will require a shortened number of increase generations and vegetative propagation of the Syn$_0$ parents.

Performance

Morphology:

The third cycle of selection of the invention for resistance to imazapic resulted in seven individuals with morphological characteristics similar to Alamo (its parent variety). However, all parental clones of the invention all have the same leaf color: a gray blue color (7.5GY, value 4/chroma 2; Munsell Color Chart for Plant Tissues, 2011). The Syn$_1$ progeny also maintain the same leaf color. All individuals have been identified at tetraploids.

PanIR was planted in two replicated field trials to compare morphological characteristics with three other lowland switchgrass varieties. The test used six replications of 20 plants of each variety at two locations: Starkville (H.H. Leveck Animal Research Center) and Brooksville (Black Belt Experiment Station). See Table 2. PanIR is derived from Alamo, so it morphologically appears similar to Alamo, but is different including the visual exception that the leaves of all seven clones are gray blue in color (7.5GY, value 4/chroma 2). In contrast, the variety Alamo has a wide range of leaf shades.

TABLE 2

Mean morphometric characteristics and cultivar description information comparing lowland switchgrass varieties Alamo, Kanlow, Espresso, and PanIR at Starkville and Brooksville, MS

| | | Mean Values from Starkville and Brooksville | | | | Third Leaf Below Apical Meristem | | Flag Leaf | | |
|---|---|---|---|---|---|---|---|---|---|---|
| | | | | Color | | | | | | Sheath |
| Cultivar | Location | Maturity --days-- | Height --cm-- | Value -7.5GY | Chroma Munsell- | Length --cm-- | Width -mm- | Length -cm- | Width -mm- | Length --cm-- |
| Alamo | SV | 202.29 | 150.50 | 4.96 | 2.14 | 41.81 | 11.16 | 39.61 | 10.37 | 13.68 |
| | BV | 197.26 | 181.47 | 5.00 | 2.00 | 52.71 | 12.46 | 49.49 | 12.44 | 15.80 |
| Mean† | | 199.78 | 165.99 | 4.98 | 2.07 | 47.26 | 11.81 | 44.55 | 11.41 | 14.74 |
| Std‡ | | 3.55 | 21.89 | 0.03 | 0.10 | 7.71 | 0.92 | 6.98 | 1.46 | 1.49 |
| Kanlow | SV | 198.52 | 165.99 | 4.98 | 2.04 | 43.69 | 12.54 | 37.75 | 11.12 | 15.92 |
| | BV | 196.59 | 178.08 | 5.00 | 2.00 | 48.51 | 13.29 | 42.26 | 12.01 | 17.18 |
| Mean | | 197.56 | 172.04 | 4.99 | 2.02 | 46.10 | 12.92 | 40.00 | 11.57 | 16.55 |
| Std | | 1.37 | 8.55 | 0.01 | 0.03 | 3.40 | 0.53 | 3.19 | 0.63 | 0.89 |
| Espresso | SV | 197.76 | 136.97 | 5.02 | 2.14 | 39.33 | 10.71 | 39.61 | 10.18 | 15.35 |
| | BV | 195.72 | 192.72 | 5.00 | 2.00 | 48.31 | 10.05 | 48.69 | 11.55 | 17.67 |
| Mean | | 196.74 | 164.84 | 5.01 | 2.07 | 43.82 | 10.38 | 44.15 | 10.87 | 16.51 |
| Std | | 1.44 | 39.42 | 0.01 | 0.10 | 6.35 | 0.47 | 6.42 | 0.97 | 1.64 |
| PanIR | SV | 200.76 | 150.59 | 5.00 | 2.16 | 42.95 | 11.49 | 43.21 | 11.22 | 14.12 |
| | BV | 196.72 | 179.17 | 5.00 | 2.00 | 53.02 | 13.19 | 50.38 | 12.46 | 16.82 |
| Mean | | 198.74 | 164.88 | 5.00 | 2.08 | 47.98 | 12.34 | 46.80 | 11.84 | 15.47 |
| Std | | 2.86 | 20.21 | 0.00 | 0.11 | 7.12 | 1.20 | 5.07 | 0.88 | 1.91 |

| Mean Values from Starkville and Brooksville | | Pubescence | | | Growth Habit | Pinicle Length | 1K Seed Weight | Total Length of 30 Seed | Total Width of 30 Seed |
|---|---|---|---|---|---|---|---|---|---|
| Cultivar | Location | Blade | Sheath | Collar | | --cm-- | --mg-- | ---mm--- | ---mm--- |
| | | ------------Scale from 0-9------------ | | | | | | | |
| Alamo | SV | 0.00 | 0.00 | 0.00 | 5.92 | 47.28 | 1216.60 | 90.07 | 34.43 |
| | BV | 0.00 | 0.00 | 0.00 | 5.89 | 53.95 | 1235.62 | | |
| Mean | | 0.00 | 0.00 | 0.00 | 5.90 | 50.62 | 1226.11 | 90.07 | 34.43 |
| Std | | 0.00 | 0.00 | 0.00 | 0.02 | 4.72 | 13.45 | 5.08 | 5.20 |
| Kanlow | SV | 0.00 | 0.00 | 0.00 | 7.16 | 42.27 | 1314.65 | 80.15 | 32.04 |
| | BV | 0.00 | 0.00 | 0.00 | 6.15 | 47.17 | 1288.70 | | |

TABLE 2-continued

| | | | | | | | | | |
|---|---|---|---|---|---|---|---|---|---|
| Mean | | 0.00 | 0.00 | 0.00 | 6.66 | 44.72 | 1301.68 | 80.15 | 32.04 |
| Std | | 0.00 | 0.00 | 0.00 | 0.71 | 3.47 | 18.35 | 1.82 | 2.11 |
| Espresso | SV | 0.00 | 0.00 | 0.00 | 6.18 | 49.14 | 1125.40 | 84.30 | 27.20 |
| | BV | 0.00 | 0.00 | 0.00 | 5.69 | 49.32 | 1230.88 | | |
| Mean | | 0.00 | 0.00 | 0.00 | 5.94 | 49.23 | 1178.14 | 84.30 | 27.20 |
| Std | | 0.00 | 0.00 | 0.00 | 0.35 | 0.13 | 74.59 | 8.13 | 2.26 |
| PanIR | SV | 0.00 | 0.00 | 0.00 | 6.05 | 52.20 | 1120.92 | 78.54 | 25.80 |
| | BV | 0.00 | 0.00 | 0.00 | 5.98 | 54.53 | 1342.12 | | |
| Mean | | 0.00 | 0.00 | 0.00 | 6.02 | 53.37 | 1231.52 | 78.54 | 25.80 |
| Std | | 0.00 | 0.00 | 0.00 | 0.05 | 1.65 | 156.41 | 7.66 | 1.53 |

[†]Mean refers to mean value at both Starkville and Brooksville
[‡]Std refers to standard deviation around the mean Evidence of Performance:

Three cycles of phenotypic recurrent selection (PRS) were used to discover resistant genotypes, polycrossing and reselecting for increased resistance to imazapic. Both controlled studies and field studies were conducted to determine the effectiveness of selection. From 2007 to 2009, screening rates of 8 oz/A twice were used for screening of seedling switchgrass ($Cycle_0$-$Cycle_1$). In 2009 and 2011, a higher rate of 14 oz/A was used in two applications to force exposure of incompletely resistant germplasm ($Cycle_1$-$Cycle_2$). During the final screening (2011-2013), a 16 oz/A rate was used to eliminate all but the most resistant genotypes ($Cycle_2$-$Cycle_3$).

Agar/Growth Chamber Germination

Since field emergence relies on soil tilth, rainfall, planter depth, and a host of other conditions, the inventors opted for a more uniform method of testing resistance: imazapic-dosed water agar. Data from germination under controlled conditions indicated significant progress for resistance to imazapic (Table 3) over three cycles of selection.

TABLE 3

Germination percentages of lowland switchgrass: Alamo ($Cycle_0$), and cycles of selection for imazapic tolerance, screened on filter paper (untreated control) and water agar + imazapic (corrected percentage germination).

| Seedlot Year | Variety or Breeding Cycle | Mean Percentage germination in untreated control | Mean Corrected percentage germination (PLS) | Screening rate of Plateau ® (imazapic) |
|---|---|---|---|---|
| 2009 | Alamo | — | 3 | 8 oz (160 g a.i./ha) |
| | PanIR $Cycle_1$ | — | 13.8 | " |
| 2010 | Alamo | 77 | 3.7 | 8 oz rate |
| | PanIR $Cycle_1$ | 67 | 3.3 | " |
| | PanIR $Cycle_2$ | 60 | 6.3 | " |
| 2011 | Alamo | 61 | 0 | 8 oz rate |
| | PanIR $Cycle_1$ | 71 | 0.7 | " |
| | PanIR $Cycle_2$ | 24 | 0.9 | " |
| 2012 | No data taken | — | — | — |
| 2013 | Alamo | 39 | 4.8 | 14 oz (280 g a.i./ha) |
| | PanIR $Cycle_1$ | 61 | 26.6 | " |
| | PanIR $Cycle_2$ | 55 | 43.5 | " |
| | PanIR $Cycle_3$ | 44 | 91.5* | " |
| 2014 | Alamo | 69 | 3.0 | 14 oz |
| | ~~PanIR $Cycle_1$~~ | — | — | " |
| | ~~PanIR $Cycle_2$~~ | — | — | " |
| | PanIR $Cycle_3$ | 71 | 94.3* | " |
| 2015 | Alamo | 7 | 0 | 16 oz |
| | ~~PanIR $Cycle_1$~~ | — | — | " |
| | ~~PanIR $Cycle_2$~~ | — | — | " |
| | PanIR $Cycle_3$ | 74 | 95.0* | " |

*indicates significant difference between Alamo ($Cycle_0$) and PanIR ($Cycle_3$) at $P < 0.001$ based on $Chi^2$ comparison.

Over the three cycles of selection, the inventors were able to raise resistance at a percentage of the population—from approximately 3% (or less) in Alamo (Cycle$_0$) to about 93.6% resistant of a 2.3 times higher rate in Cycle$_3$ (PanIR) as measured under controlled conditions.

Field Emergence

Data indicating field testing performance is provided in Tables 3 and 4. Plants were seeded in July and August of 2014 and during May of 2015. Data presented in Table 4 indicates 2014 testing at three locations (Brooksville, Newton, and Starkville). Table 5 presents data from two locations (Brooksville and Starkville). At all locations, PanIR seedling numbers exceeded all other generations of selection as well as the resistant check (indiangrass).

TABLE 4

Number of seedlings surviving a 14 oz/A application of imazapic at three locations in Mississippi (2014).

| Location | Variety | 42 days after spraying |
|---|---|---|
| Brooksville | Indiangrass (resistant check) | 16.25†B* |
| | Rapid Germ Switchgrass | 2.75 B |
| | Alamo (Cycle 0) | 2.00 B |
| | Cycle 1 | 8.25 B |
| | Cycle 2 | 14.25 B |
| | PanIR (Cycle 3)* | 53.00 A |
| Newton | Indiangrass (resistant check) | 14.50 B |
| | Rapid Germ Switchgrass | 2.00 B |
| | Alamo (Cycle 0) | 6.50 B |
| | Cycle 1 | 10.25 B |
| | Cycle 2 | 13.00 B |
| | PanIR (Cycle 3)* | 43.00 A |
| Starkville | Indiangrass (resistant check) | 19.75 B |
| | Rapid Germ Switchgrass | 2.00 C |
| | Alamo (Cycle 0) | 8.25 BC |
| | Cycle 1 | 3.25 C |
| | Cycle 2 | 13.75 BC |
| | PanIR (Cycle 3)* | 49.50 A |

†Mean number of seedlings emerged per 30 cm of row. Mean calculated from four replications and four randomly selected locations per plot per replication (n = 12).
*Means followed by the same letter are not significantly difference at alpha of 0.05 within location.

TABLE 5

Number of seedlings surviving a 14 oz/A application of imazapic at two locations in Mississippi (2015).

| Location | Variety | 42 days after spraying |
|---|---|---|
| Brooksville | Indiangrass (resistant check) | 24.50†B* |
| | Rapid Germ Switchgrass | 0.00 C |
| | Alamo (Cycle 0) | 5.75 BC |
| | Cycle 1 | 19.25 BC |
| | Cycle 2 | 18.75 BC |
| | PanIR (Cycle 3)* | 115.75 A |
| Starkville | Indiangrass (resistant check) | 13.33 B |
| | Rapid Germ Switchgrass | 1.00 B |
| | Alamo (Cycle 0) | 1.00 B |
| | Cycle 1 | 2.00 B |
| | Cycle 2 | 5.67 B |
| | PanIR (Cycle 3)* | 16.00 A |

†Mean number of seedlings emerged per 30 cm of row. Mean calculated from four replications and four randomly selected locations per plot per replication (n = 12).
**Means followed by the same letter are not significantly difference at alpha of 0.05 within location.

Biomass Yield

Dry matter biomass yield of PanIR at Starkville, Miss. is shown in Table 6. No significant differences were observed in yield between imazapic resistant and susceptible switchgrass varieties (PanIR, BoMaster, and Robusto, respectively), due to high variability between test plots.

TABLE 6

Lowland switchgrass and indiangrass forage dry matter yields planted after a 16 oz/A Plateau rate 18 months earlier for 2015 at Starkville, MS.

| | | Yield | |
|---|---|---|---|
| Species | Variety | kg/2 m row | kg/ha |
| Lowland switchgrass | BoMaster | 0.1000 | 103.20 |
| Lowland switchgrass | PanIR | 0.5963 | 615.38 |
| Indiangrass (check) | IG Cycle 7 rapid germ | 0.2338 | 241.28 |
| Upland switchgrass | Robusto | 0.37385 | 385.81 |
| LSD$_{0.05}$ | | 0.5082 | 524.46 |

All parameters presented herein including, but not limited to, sizes, dimensions, times, temperatures, pressures, amounts, distances, quantities, ratios, weights, volumes, percentages, and/or similar features and data and the like, for example, represent approximate values and can vary with the possible embodiments described and those not necessarily described but encompassed by the invention.

The terms "a", "an", "the" and similar terms used in describing the present invention concerning any particular item, component, material, or product and as used in the claims are defined as at least one and could be more than one and are to be construed to encompass the singular and the plural, unless otherwise indicated or clearly contradicted by the context of use. Further, the terms "comprising", "containing", "including", and "having" are to be construed as open-ended terms meaning "including, but not limited to,", unless otherwise noted. Still further, ranges of values are intended to serve as a method of referring to each separate value falling in or within the range, unless otherwise noted, and each separate value is hereby incorporated herein as if individually recited (i.e., if the range 20-25 is disclosed, then 21, 22, 23, and 24 are likewise disclosed). Any methods disclosed can be performed in any suitable order, unless otherwise indicated or clearly contradicted by the context. The use of examples or exemplary language (i.e, "such as") is intended to explain the present invention and does not present a limitation on the scope of the invention. Nothing in the specification should be construed as indicating that any non-claimed element is essential to the practice of the invention.

Deposit Information

A sample of the new switchgrass cultivar designated PanIR disclosed herein and recited in the appended claims is kept and maintained at the Mississippi State University Agricultural Experiment Station. In addition, a sample of the seed of the invention has been deposited with the American Type Culture Collection (ATCC), 10801 University Boulevard, Manassas, Va. 20110-2209, United States of America, on Mar. 31, 2020, and was assigned ATCC Accession No. PTA-126739.

To satisfy the enablement requirements of 35 U.S.C. § 112, and to certify that the deposit of the present invention meets the criteria set forth in 37 C.F.R. §§ 1.801-1.809 and Manual of Patent Examining Procedure (MPEP) 2402-2411.05, Applicants hereby make the following statements regarding the deposited material of switchgrass cultivar PanIR:

If the deposit is made under the terms of the Budapest Treaty, the invention will be irrevocably and without restriction released to the public upon the granting of a patent.

If the deposit is made not under the terms of the Budapest Treaty, Applicant(s) provides assurance of compliance by the following statements:
1. During the pendency of this application, access to the invention will be afforded to the Commissioner upon request;
2. All restrictions on availability to the public will be irrevocably removed upon granting of the patent under conditions specified in 37 C.F.R. § 1.808;
3. The deposit will be maintained in a public repository for a period of 30 years or 5 years after the last request or for the effective life of the patent, whichever is longer;
4. A test of the viability of the biological material at the time of deposit will be conducted by the public repository under 37 C.F.R. § 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon granting of any claims in this application, all restrictions on the availability to the public of the variety will be irrevocably removed by affording access to a deposit of at least 625 seeds of the same variety with the ATCC.

The above detailed description is presented to enable any person skilled in the art to make and use the invention. Specific details have been revealed to provide a comprehensive understanding of the present invention, and are used for explanation of the information provided. These specific details, however, are not required to practice the invention, as is apparent to one skilled in the art. Descriptions of specific applications, analyses, and/or calculations are meant to serve only as representative examples. Various modifications to the preferred embodiments may be readily apparent to one skilled in the art, and the general principles defined herein may be applicable to other embodiments and applications while still remaining within the scope of the invention. There is no intention for the present invention to be limited to the embodiments shown and the invention is to be accorded the widest possible scope consistent with the principles and features disclosed herein.

A number of exemplary embodiments and aspects have been discussed herein and those skilled in the art will recognize certain modifications, permutations, additions, and combinations thereof. It is intended that the claims herein are interpreted to include all such modifications, permutations, additions, and combinations that are within their scope.

While various embodiments of the present invention have been described above, it should be understood that they have been presented by way of example and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above-described exemplary embodiments.

The compositions, processes, devices, products, apparatus, designs, systems, configurations, and/or methods of the present invention are often best practiced by empirically determining the appropriate values of the operating parameters or by conducting simulations to arrive at best design for a given application. Accordingly, all suitable modifications, combinations, and equivalents should be considered as falling within the spirit and scope of the invention.

INCORPORATION BY REFERENCE

All references, articles, publications, patents, patent publications, and patent applications that may have been cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

American Cyanamid Company. 2000. Plateau herbicide, for weed control, native grass establishment and turf growth suppression on roadsides and other non-crop areas. PE-47015. Parsippany, N.J.

Bahler, C. C., K. P. Vogel, and L. E. Moser. 1983. Atrazine tolerance in warm-season grass seedlings. Agron. J. 76:891-895.

Baker, R. D., L. B. McCarty, D. L. Colvin, J. M. Higgins, J. S. Weinbrecht, and J. E. Moreno. 1999. Bahiagrass (*Paspalum nutatum*) seedhead suppression following consecutive yearly applications of plant growth retardants. Weed Tech.13: 378-384.

Drexel Chemical Company. 2007. Simazine 90DF herbicide, for weed control in certain crops and ornamental plantings. 19713-252. Memphis, Tenn.

Fick, W. H. and D. E. Peterson. 1995. Musk thistle identification and control. Kansas State Univ. Coop. Ext. Serv. Publ. L-231. Kansas State Univ., Manhattan.

Foes, M. J., L. Liu, G. Vigue, E. W. Stoller, L. M. Wax and P. J. Tranel. 1999. A Kochia (*Kochia scoparia*) biotype resistant to triazine and ALS-inhibiting herbicides. Weed Sci. 47:20-27. In Tranel, P. J., and T. R. Wright. 2002. Resistance of weeds to ALS-inhibiting herbicides: what have we learned? Weed Science 50:700-712.

Franssen, A. S., D. Z. Skinner, K. Al-Khatib, M. J. Horak, and P. A. Kulakow. 2001. Interspecific hybridization and gene flow of ALS resistance in *Amaranthus* species. Weed Sci. 49:598-606.

Grabowski, Janet. 2002. Response of Native Wildflowers and Grasses to Postemergence Herbicides. Technical Report. Jamie L. Whitten Plant Materials Center, Coffeeville, Miss. Vol. 16 No. 7.

Harper, C. A., G. D. Morgan, and C. E. Dixon. 2004. Establishing Native Warm-Season Grasses using Conventional and No-till Technology with Various Applications of Plateau® Herbicide pg. 63-70. In Johnny Randall and Joseph C. Burns (eds.) Proceedings of the Third Eastern Native Grass Symposium. The North Carolina Botanical Garden, Chapel Hill, N.C., Oct. 1-3, 2002. Ominipress. Madison, Wis.

Harper, Craig. 2007. Native Warm-Season Grasses: Identification, Establishment and Management for Wildlife and Forage Production in the Mid-South. University of Tennessee Extention. Knoxville, Tenn.

Hart, S. E., J. W. Saunders, and D. Penner. 1993. Semidominant nature of monogenic sulfonylurea herbicide resistance in sugarbeet (*Beta vulgaris*). Weed Sci. 41:317-324. In Tranel, P. J., and T. R. Wright. 2002. Resistance of weeds to ALS-inhibiting herbicides: What have we learned? Weed Science 50:700-712.

Helena Chemical Company. 2007. Atrazine 4L herbicide, for season-long weed control in corn and sorghum for weed control in certain other crops and industrial sites., 5905-470. Collierville, Tenn.

Jasieniuk, M., A. L. Brule-Babel, and I. N. Morrison. 1994. Inheritance of trifluralin resistance in green foxtail (*Setaria viridis*). Weed Sci. 42:123-127. In Tranel, P. J., and T. R. Wright. 2002. Resistance of weeds to ALS-inhibiting herbicides: what have we learned? Weed Science 50:700-712.

Jiang, W. and P. J. Tranel. 2002. Variability in a herbicide target-site gene. Weed Sci. Soc. Am. Abstr. 42:20. In Tranel, P. J., and T. R. Wright. 2002. Resistance of weeds to ALS-inhibiting herbicides: what have we learned? Weed Science 50:700-712.

Martinez-Reyna, J. M. and K. P. Vogel. 2002. Incompatibility systems in switchgrass. Crop Sci. 42:1800-1805.

Mitchell, Rob and Britton, Carlton. 2000. Managing Weeds to Establish and Maintain Warm-Season Grasses. pp. 159-173. In Moore, K. J. and B. E. Anderson (eds) Native Warm-Season Grasses: Research Trends and Issues. CSSA Special Pub. No. 30. Madison, Wis.

Munsell® Color Chart for Plant Tissues. 2011. Munsell® Color Chart for Plant Tissues with genuine Munsell® color chips. Grand Rapids, Mich.

Perez-Jones, A., K. W. Park, N. Polge, J. Colquhoun, and C. A. Mallory-Smith. 2007. Investigating the mechanisms of glyphosate resistance in *Lolium multiflorum*. Planta. 226:395-404.

Salon, P. R. and M. van der Grinten. 1997. Eastern Gamagrass Response to Accent (nicosulfuron), Basis (rimsulfuron), and Plateau (imazapic) Herbicides in Comparison to a few Common Corn Herbicides. Big Flats Plant Materials Center, Corning, N.Y.

Sebastian, S. A., G. M. Fader, J. F. Ulrich, D. R. Forney, and R. S. Chaleff. 1989. Semi-dominant soybean mutation for resistance to sulfonylurea herbicides. Crop Sci. 29:1403-1408. In Tranel, P. J., and T. R. Wright. 2002. Resistance of weeds to ALS-inhibiting herbicides: what have we learned? Weed Science 50:700-712.

Tan, S., R. R. Evans, M. L. Dahmer, B. K. Singh, and D. L. Shaner. 2005. Imidazolinone-tolerant crops: History, current status, and future. Pest Manag. Sci. 61:246-257.

Tranel, P. J., and T. R. Wright. 2002. Resistance of weeds to ALS-inhibiting herbicides: what have we learned? Weed Science 50:700-712.

Tu et al. 2004. Imazapic. Weed Control Methods Handbook. The Nature Conservancy.

Van Eerd, L. L., M. D. McLean, G. R. Stephenson, and J. C. Hall. 2004. Resistance to quinclorac and ALS-inhibitor herbicides in *Galium spurium* is conferred by two distinct genes. Weed Res. 44:355-365.

Warren, L. S. and H. D. Coble. 1999. Managing purple nutsedge (*Cyperus rotundus*) populations utilizing herbicide strategies and crop rotation sequences. Weed Tech. 13: 494-503.

Washburn, B. E. and T. G. Barnes. 2000. Postemergence tall fescue (*Festuca arundinacia*) control at different growth stages with glyphosate and AC 263,222. Weed Tech. 13:494-503.

Wilcut, J. W., J. S. Richburg, and F. R. Walls. 1999. Response of Johnsongrass (*Sorghum halepence*) and imidazolinone-resistant corn (*Zea mays*) to AC 263,222. Weed Tech. 13:484-488.

Wright, T. R. and D. Penner. 1998. Corn (*Zea mays*) acetolactate synthase sensitivity to four classes of ALS-inhibiting herbicides. Weed Sci. 46:8-12.

Zeng, L. and W. V. Baird. 1997. Genetic basis of dinitroaniline herbicide resistance in a highly resistant biotype of goosegrass (*Eleusine indica*). J. Hered. 88:427-432. In Tranel, P. J., and T. R. Wright. 2002. Resistance of weeds to ALS-inhibiting herbicides: what have we learned? Weed Science 50:700-712.

What is claimed is:

1. A seed of switchgrass cultivar PanIR, wherein a representative sample of switchgrass seed of said cultivar has been deposited under ATCC Accession No. PTA-126739.

2. A switchgrass plant, or a part thereof, produced by growing the seed of claim 1.

3. A commodity plant product comprising the switchgrass plant of claim 2, or a part thereof.

4. The switchgrass plant of claim 2, wherein the switchgrass plant is resistant to an imidazolinone herbicide at a level of herbicide that typically inhibits the growth of a switchgrass plant.

5. The switchgrass plant of claim 4, wherein the imidazolinone herbicide is imazapic.

6. A switchgrass plant, or a part thereof, having all of the characteristics of switchgrass cultivar PanIR and having all of the physiological and morphological characteristics of the switchgrass cultivar PanIR listed in Table 2, wherein a representative sample of seed of said switchgrass cultivar PanIR has been deposited under ATCC Accession No. PTA-126739.

7. A method of producing switchgrass plants, said method comprising planting a plurality of switchgrass seeds as recited in claim 1 under conditions favorable for growing switchgrass plants.

8. The method of claim 7, further comprising producing switchgrass seed from the resultant switchgrass plants.

9. A switchgrass seed produced by the method of claim 8.

10. Pollen of the plant of claim 2.

11. An ovule of the plant of claim 2.

12. The method of claim 7, further comprising applying an imidazolinone herbicide near the switchgrass plants to control weeds and undesirable plants, wherein the herbicide typically inhibits the enzyme acetohydroxytacid synthase (AHAS), at a level that typically inhibits the growth of a switchgrass plant.

13. The method of claim 12, wherein the imidazolinone herbicide is imazapic.

14. A tissue culture of regenerable cells or protoplasts produced from the switchgrass plant of claim 2, wherein a plant regenerated from the tissue culture has all of the physiological and morphological characteristics of the switchgrass cultivar PanIR listed in Table 2 and wherein a representative sample of seed of switchgrass cultivar PanIR has been deposited under ATCC Accession No. PTA-126739.

15. The tissue culture of claim 14, wherein said regenerable cells or protoplasts are produced from a plant part tissue selected from the group consisting of embryos, meristematic cells, pollen, cotyledon, hypocotyl, leaves, anthers, roots, root tips, pistils, flowers, seeds, glumes, panticles, and stems.

16. A protoplast produced from the tissue culture of claim 15.

17. A switchgrass plant, or a part thereof, having all of the physiological and morphological characteristics of the switchgrass plant of claim 4 and the imidazolinone herbicide resistance characteristics of the switchgrass cultivar PanIR.

18. A switchgrass plant regenerated from the tissue culture of claim 15, wherein the plant has all of the physiological and morphological characteristics of the switchgrass cultivar PanIR listed in Table 2 and the imidazolinone herbicide resistance characteristics of the switchgrass cultivar PanIR, and wherein a representative sample of seed of said switchgrass cultivar PanIR has been deposited under ATCC Accession No. PTA-126739.

19. A method of producing a seven-parent synthetic hybrid imazapic resistant switchgrass seed, the method comprising crossing a first parent switchgrass plant with a second parent switchgrass plant and harvesting the resultant hybrid switchgrass seed; wherein the first parent switchgrass plant is a switchgrass plant of switchgrass cultivar PanIR of claim 2 and the second parent switchgrass plant is one of the other six PanIR parents; wherein a representative sample of switchgrass seed of switchgrass cultivar PanIR has been deposited under ATCC Accession No. PTA-126739; and wherein resultant hybrid switchgrass progeny plants are grown from said hybrid switchgrass seed and retain the characteristic of resistance to the imidazolinone herbicide imazapic at a level that typically inhibits the growth of a switchgrass plant.

20. Hybrid switchgrass seed produced by the method of claim 19, wherein the hybrid progeny has all of the physiological and morphological characteristics of the switchgrass cultivar PanIR as listed in Table 2 and the imidazolinone herbicide resistance characteristics of the switchgrass cultivar PanIR.

21. A hybrid switchgrass progeny plant, or a part thereof, produced by growing said hybrid switchgrass seed of claim 20, wherein said progeny plant retains the characteristic of resistance to the imidazolinone herbicide imazapic at a level that typically inhibits the growth of a switchgrass plant.

22. The method of claim 19, further comprising crossing the resultant hybrid switchgrass progeny plants with the switchgrass cultivar PanIR to produce new progeny plants, and optionally repeating one or more times said crossing in succession to produce selectively higher progeny plants that retain all of the physiological and morphological characteristics of the switchgrass cultivar PanIR listed in Table 2 and the imidazolinone herbicide resistance characteristics of the switchgrass cultivar PanIR.

23. A plant produced by the method of claim 22, wherein the plant has all of the physiological and morphological characteristics of the switchgrass cultivar PanIR as listed in Table 2 and the imidazolinone herbicide resistance characteristics of the switchgrass cultivar PanIR.

24. A method of producing a switchgrass cultivar plant derived from the switchgrass cultivar PanIR, the method comprising the step of crossing the plant of claim 2 with a second switchgrass plant to produce a progeny plant derived from the switchgrass cultivar PanIR.

25. The method of claim 24, further comprising the steps of:
(a) crossing the progeny plant derived from the switchgrass cultivar PanIR with itself or a second switchgrass plant to produce a seed of progeny plant of a subsequent generation;
(b) growing the progeny plant of the subsequent generation from the seed;
(c) crossing the progeny plant of the subsequent generation with itself or a second switchgrass plant to produce a switchgrass plant derived from the switchgrass cultivar PanIR; and
(d) repeating steps (a) and (b) for at least 1 more generation to produce a switchgrass plant further derived from the switchgrass cultivar PanIR as listed in Table 2.

26. A method of introducing the desired trait of imazapic resistance into a switchgrass plant, the method comprising:
(a) crossing a switchgrass cultivar PanIR plant grown from switchgrass cultivar PanIR seed, wherein a representative sample of seed has been deposited under ATCC Accession No. PTA-126739, with another switchgrass plant that comprises the desired trait of imazapic resistance to produce F1 progeny plants;
(b) selecting one or more progeny plants that have the desired trait of imazapic resistance to produce selected progeny plants;
(c) crossing the progeny plants with the switchgrass cultivar PanIR plants to produce backcross progeny plants;
(d) selecting the backcross progeny plants that have the desired trait of imazapic resistance and all of the physiological and morphological characteristics of the switchgrass cultivar PanIR as listed in Table 2 to produce selected progeny plants; and
e) repeating steps (c) and (d) three or more times in succession to produce selected fourth or higher backcross progeny plants that comprise the desired trait of imazapic resistance and all of the physiological and morphological characteristics of the switchgrass cultivar PanIR as listed in Table 2.

27. A method of producing a commodity plant product, the method comprising obtaining the switchgrass plant of claim 2, or a part thereof, and producing the commodity plant product from said plant or part thereof, wherein said commodity plant product is selected from the group consisting of biofuel feedstock, grass restoration material, and landscape material.

* * * * *